US00PP18156P2

(12) United States Plant Patent
Hooijman

(10) Patent No.: US PP18,156 P2
(45) Date of Patent: Oct. 30, 2007

(54) ***GYPSOPHILA* PLANT NAMED 'ESM CIRQUE'**

(50) Latin Name: *Gypsophila hybrida*
Varietal Denomination: Esm Cirque

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/444,243

(22) Filed: May 31, 2006

(51) Int. Cl.
*A01H 5/00* (2006.01)

(52) U.S. Cl. ..... Plt./354
(58) Field of Classification Search ..... Plt./354
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Gypsophila* plant named 'Esm Cirque', characterized by its erect and strong flowering stems; early, uniform and freely flowering habit; double luminous white-colored flowers; and good postproduction longevity.

1 Drawing Sheet

Botanical designation: *Gypsophila hybrida.*
Cultivar denomination: 'Esm Cirque'.

BACKGROUND OF THE INVENTION

The present invention relates to a new and distinct cultivar of *Gypsophila* plant, botanically known as *Gypsophila hybrida,* grown commercially as a cut flower, and hereinafter referred to by the name 'Esm Cirque'.

The new *Gyposphila* is a product of a planned breeding program conducted by the Inventor in El Quinche, Pichincha, Ecuador. The objective of the breeding program is to create new freely flowering *Gyposphila* cultivars with many petals per flower and straight stems.

The new *Gypsophila* originated from a cross-pollination made by the Inventor in El Quinche, Pichincha, Ecuador in August, 2003 of a proprietary selection of *Gypsophila hybrida* identified as Line 114, not patented, as the female, or seed, parent with a proprietary selection of *Gypsophila hybrida* identified as Line 56, not patented. The cultivar Esm Cirque was discovered and selected by the Inventor as a flowering plant from within the progeny of the state cross-pollination in a controlled environment in El Quinche, Pichincha, Ecuador.

Asexual reproduction of the new *Gyposphila* by cuttings in a controlled environment in El Quinche, Pichincha, Ecuador since August, 2004, has shown that the unique features of this new *Gypsophila* are stable and reproduced true to type in successive generations.

SUMMARY OF THE INVENTION

The cultivar Esm Cirque has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Cirque'. These characteristics in combination distinguish 'Esm Cirque' as a new and distinct cultivar of *Gypsophila:*

1. Erect and strong flowering stems.
2. Early, uniform and freely flowering habit.

3. Double luminous white-colored flowers.
4. Good postproduction longevity.

In side-by-side comparisons conducted in El Quinche, Pichincha, Ecuador, plants of the new *Gypsophila* differed from plants of the female parent selection in the following characteristics:

1. Plants of the new *Gypsophila* flowered earlier than plants of the female parent selection.
2. Plants of the new *Gypsophila* had larger flowers than plants of the female parent selection.
3. Flowers of plants of the new *Gypsophila* had more petals than flowers of plants of the female parent selection.

In side-by-side comparisons conducted in El Quinche, Pichincha, Ecuador, plants of the new *Gypsophila* differed from plants of the male parent selection in the following characteristics:

1. Plants of the new *Gypsophila* had stronger flowering stems than plants of the male parent selection.
2. Plants of the new *Gypsophila* had smaller flowers than plants of the male parent selection.

Plants of the new *Gypsophila* can be compared to plants of the *Gypsophila* cultivar New Hope, not patented. In side-by-side comparisons conducted in El Quinche, Pichincha, Ecuador, plants of the new *Gypsophila* differed from plants of the cultivar New Hope in the following characteristics:

1. Plants of the new *Gypsophila* had shorter internodes than plants of the cultivar New Hope.
2. Plants of the new *Gypsophila* had shorter, but broader leaves than plants of the cultivar New Hope.
3. Plants of the new *Gypsophila* flowered earlier and more freely than plants of the cultivar New Hope.
4. Plants of the new *Gypsophila* did not produce seeds and fruits whereas plants of the cultivar New Hope produced seeds and fruits.

BRIEF DESCRIPTION OF THE PHOTOGRAPHS

The accompanying photographs illustrate the overall appearance of the new *Gypsophila.* These photographs show the colors as true as it is reasonably possible to obtain in colored reproductions of this type. Colors in the photographs may differ slightly from the color values cited in the detailed botanical description which accurately describe the colors of the new *Gypsophila*.

The photograph at the top of the first sheet comprises a side perspective view of a typical flowering stem of 'Esm Cirque'.

The photograph at the bottom of the sheet is a close-up view of typical flowers of 'Esm Cirque'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown during the winter in El Quinche, Pichincha, Ecuador in ground beds in an outdoor nursery and under conditions and practices which approximate those generally used in commercial cut *Gypsophila* production. During the production of the plants, day temperatures ranged from 11° C. to 28° C. and night temperatures ranged from 5° C. to 11° C. Plants were pinched one time about five weeks after planting and were grown under long day/short day conditions. Measurements and numerical values represent averages for typical four-month old flowering plants.

Botanical classification: *Gypsophila hybrida* cultivar Esm Cirque.

Commercial classification: Cut flower *Gypsophila*.

Parentage:

*Female, or seed, parent.*—Proprietary selection of *Gypsophila hybrida* identified as Line 114, not patented.

*Male, or pollen, parent.*—Proprietary selection of *Gypsophila hybrida* identified as Line 56, not patented.

Propagation:

*Type.*—By cuttings.

*Time to initiate roots.*—About 16 to 21 days at 17° C. to 25° C.

*Time to produce a rooted cutting.*—About five to six weeks at 17° C. to 25° C.

*Root description.*—Fine; 158A in color.

*Rooting habit.*—Freely branching.

Plant description:

*Appearance.*—Perennial cut flower. Erect and strong flowering stems; inverted triangle form. Freely flowering; many-petalled luminous white-colored flowers arranged in symmetrical and moderately dense compound cymes. Vigorous growth habit.

*Branching habit.*—After pinching, about 20 flowering stems develop per year.

*Plant height.*—about 111 cm.

*Plant diameter or spread.*—About 112 cm.

*Flowering stems.*—Length: About 106 cm. Diameter: About 5.4 mm. Internodes length: About 4.9 cm. Strength: Moderately strong. Texture: Glabrescent. Color: 146B.

Foliage description:

*Arrangement.*—Opposite, decussate, simple; sessile.

*Length.*—about 7.9 cm.

*Width.*—About 2.2 cm.

*Shape.*—Lanceolate.

*Apex.*—Acute.

Base.—Cuneate.

*Margin.*—Entire.

*Texture, upper and lower surfaces.*—Smooth, glabrous; waxy.

*Venation pattern.*—Parallel.

*Color.*—Developing foliage, upper surface: 139A to 147A. Developing foliage, lower surface: 139A. Fully expanded foliage, upper surface: 147A to 139A; venation, 147A. Fully expanded foliage, lower surface: 147A; venation, 137A.

Flower description:

*Flower arrangement and habit.*—Symmetrical compound cymes with numerous many-petalled luminous white-colored flowers, flowers rotate. Very freely flowering, about 2,250 flowers develop per inflorescence. Flowers face mostly upright.

*Flowering response.*—In Ecuador, plants flower year round. Plants begin flowering about 12 weeks after planting.

*Post-production longevity.*—As a cut flower, flowers last for about 13 days. Flowers persistent.

*Fragrance.*—Slightly fragrant; pleasant.

Inflorescence height.—About 78 cm.

*Inflorescence diameter.*—About 62 cm.

*Flower diameter.*—About 1.1 cm.

*Flower depth (height).*—About 7 mm.

*Flower buds.*—Length: About 3 mm. Diameter: About 3 mm. Shape: Nearly globose. Color: 144D.

*Petals/petaloids.*—Quantity per flower: About 38 arranged in clusters. Length: About 5.5 mm. Width: About 2.6 cm. Shape: Oval to spatulate. Apex: Truncate to emarginate. Margin: Entire. Texture, upper and lower surfaces: Smooth, glabrous; waxy. Color: When opening and fully opening, upper surface: Close to 155D; color becoming closer to 155A with development. When opening and fully opening, lower surface: Close to 155D.

*Sepals.*—Quantity per flower: About five fused to form a cup-shaped calyx. Length: About 3.4 mm. Width: About 2.4 mm. Shape: Roughly linear. Apex: Acute. Margin: Entire. Texture, upper and lower surfaces: Smooth, glabrous. Color: When developing, upper surface: 143C. When developing, lower surface: 146A; towards the apex, 187D. Fully developed, upper surface: 143C; towards the apex, 137A. Fully developed, lower surface: 147A.

*Peduncles.*—Length: About 3.4 cm. Diameter: About 4 mm. Strength: Moderately strong. Angle: About 43° from vertical. Texture: Smooth, glabrous. Color: 146B.

*Pedicels.*—Length: About 8.6 mm. Diameter: About 2.5 mm. Strength: Moderately strong. Angle: About 57° from vertical. Texture: Smooth, glabrous. Color: 146A.

*Reproductive organs.*—Stamens: Quantity per flower: Five. Anther shape: Reniform to globose. Anther length: Less than 1 mm. Anther color: 155B to 161C. Pollen amount: Scarce. Pollen color: Close to 155B to 161C. Pistils: Quantity per flower: One. Pistil length: About 8 mm. Style length: About 6 mm. Style color: Close to 155D. Stigma shape: Curved apiculate. Stigma color: Close to 155D. Ovary color: 143C. Seed/fruit: Seed and fruit production has not been observed.

Disease/pest resistance: Plants of the new *Gypsophila* have not been shown to be resistant to pathogens and pests common to *Gypsophila*.

Temperature tolerance: Plants of the new *Gypsophila* have been observed to tolerate temperatures ranging from about 7° C. to about 30° C.

It is claimed:

1. A new and distinct *Gypsophila* plant named 'Esm Cirque' as illustrated and described.

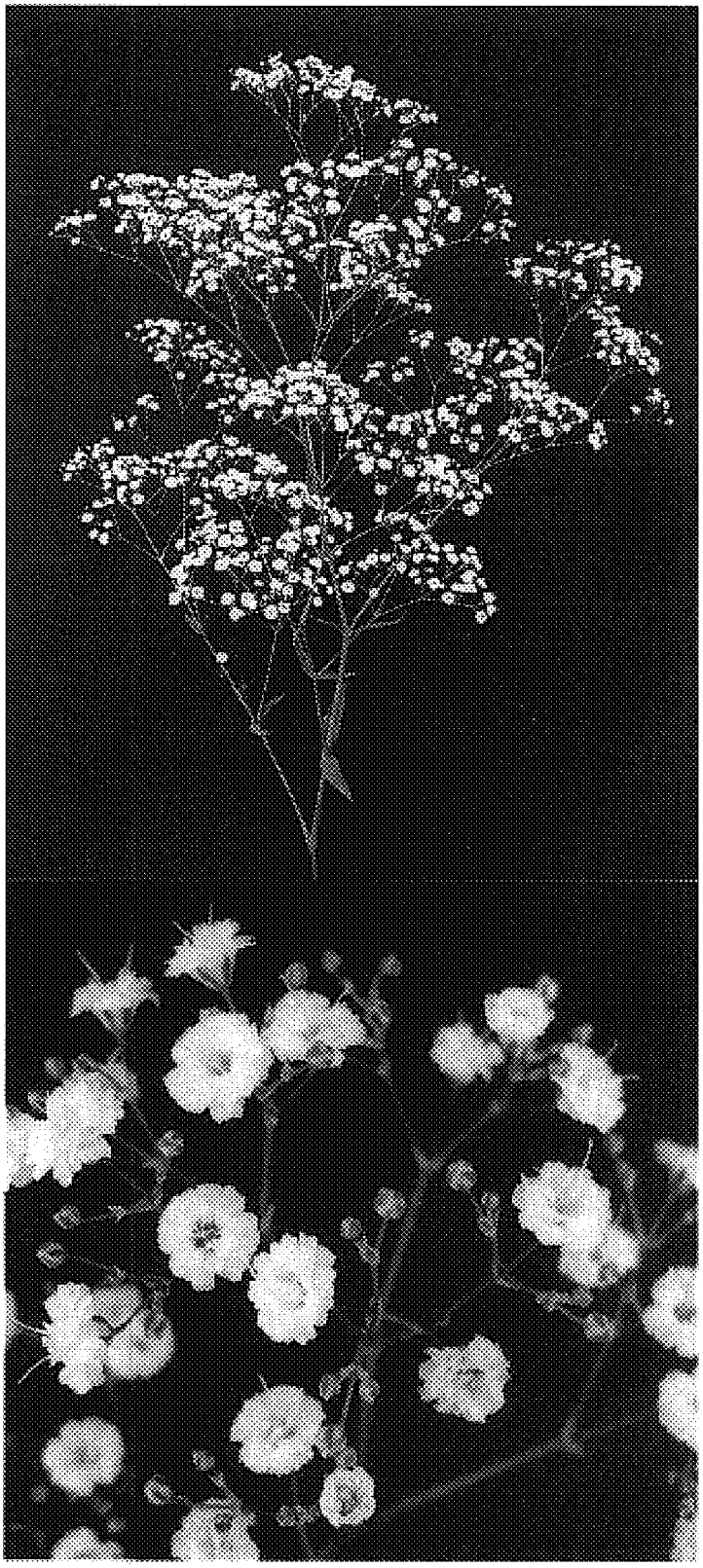

* * * * *